US009204896B2

(12) United States Patent
Williams

(10) Patent No.: US 9,204,896 B2
(45) Date of Patent: Dec. 8, 2015

(54) INSTRUMENT FOR REMOVAL OF MATERIAL FROM WITHIN A BODY

(75) Inventor: Lawrence Williams, Valley Center, CA (US)

(73) Assignee: ALPHATEC SPINE, INC., Carlsbad, CA (US)

( * ) Notice: Subject to any disclaimer, the term of this patent is extended or adjusted under 35 U.S.C. 154(b) by 564 days.

(21) Appl. No.: 13/545,174

(22) Filed: Jul. 10, 2012

(65) Prior Publication Data

US 2013/0018377 A1    Jan. 17, 2013

Related U.S. Application Data

(60) Provisional application No. 61/507,767, filed on Jul. 14, 2011.

(51) Int. Cl.
| | | |
|---|---|---|
| *A61B 17/32* | (2006.01) | |
| *A61B 17/56* | (2006.01) | |
| *A61B 17/14* | (2006.01) | |
| *A61B 17/16* | (2006.01) | |

(52) U.S. Cl.
CPC ............... *A61B 17/56* (2013.01); *A61B 17/14* (2013.01); *A61B 17/16* (2013.01); *A61B 17/1659* (2013.01); *A61B 17/1671* (2013.01); *A61B 2017/143* (2013.01); *A61B 2017/145* (2013.01); *A61B 2017/564* (2013.01)

(58) Field of Classification Search
CPC .................... A61B 17/1604; A61B 2017/1602; A61B 17/1615; A61B 17/14; A61B 2017/143; A61B 2017/145; A61B 17/16; A61B 17/1659; A61B 17/1671; A61B 17/56; A61B 2017/564; B27B 17/14
See application file for complete search history.

(56) References Cited

U.S. PATENT DOCUMENTS

| | | | |
|---|---|---|---|
| 6,280,450 B1 * | 8/2001 | McGuckin, Jr. ............... | 606/114 |
| 6,746,451 B2 * | 6/2004 | Middleton et al. .............. | 606/79 |
| 7,674,265 B2 * | 3/2010 | Smith et al. ..................... | 606/79 |
| 8,021,379 B2 * | 9/2011 | Thompson ..... A61B 17/320758 | 606/128 |
| 8,398,640 B2 * | 3/2013 | Hawkins ............ A61B 17/1624 | 30/381 |
| 8,562,607 B2 * | 10/2013 | Truckai et al. ................... | 606/79 |
| 8,961,518 B2 * | 2/2015 | Taylor et al. .................... | 606/79 |
| 2007/0149990 A1 * | 6/2007 | Palmer et al. ................... | 606/167 |
| 2008/0294166 A1 * | 11/2008 | Goldin et al. .................... | 606/79 |
| 2010/0161060 A1 * | 6/2010 | Schaller et al. ............ | 623/17.16 |
| 2011/0184447 A1 * | 7/2011 | Leibowitz et al. ............. | 606/170 |
| 2012/0172907 A1 * | 7/2012 | Lee Shee et al. ............. | 606/190 |

FOREIGN PATENT DOCUMENTS

FR        2886839 A1 * 12/2006  ......... A61B 17/1617

OTHER PUBLICATIONS

Machine Translation of FR 2886839 retrieved from <http://translationportal.epo.org/emtp/translate/?ACTION=description-retrieval&COUNTRY=FR&ENGINE=google&FORMAT=docdb&KIND=A1&LOCALE=en_EP&NUMBER=2886839&OPS=ops.epo.org/3.1&SRCLANG=fr&TRGLANG=en> on Oct. 6, 2015.*

* cited by examiner

*Primary Examiner* — Larry E Waggle, Jr.
(74) *Attorney, Agent, or Firm* — Michael J. Loi

(57) ABSTRACT

An instrument for removing material from within the body includes a distal portion that includes an adjustable length relative to a proximal portion and a flexible member that circulates through the distal portion. The exposed portion of the flexible member extends from the distal portion to remove the material.

18 Claims, 4 Drawing Sheets

INSTRUMENT FOR REMOVAL OF MATERIAL FROM WITHIN A BODY

FIELD

The present invention relates to devices and methods for removing material from within a body, particularly an instrument and method for removing material from an intervertebral disc, such as in a discectomy.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

Various techniques are known for performing minimal-invasive discectomy. Most commonly, conventional cutting and manipulation tools are used under endoscopic control to sever disc tissue and remove it through a working channel. This approach is slow and tedious, particularly given limitations on the size of incision, and the risk of damage to the dural sac or nerve roots. Tools that use cutting and suction commonly require cleaning, sanitizing, and maintenance that increases costs associated with the procedures.

U.S. Patent Application Publication No. 2007/0149990 to Palmer et al. proposes a tissue removal instrument in which an elongated hollow device is formed from shape-memory materials that is biased to a predefined coiled form. The device has lateral cutting openings into which tissue is meant to be drawn under the influence of suction. The device is not sufficiently rigid to define a predictable path, and is described as loosening, tearing, or disrupting tissue within the nucleus of the disc during insertion. The unpredictability of the path that will be followed by the Palmer device during insertion may lead to a risk of perforation and injury and may incur difficulty reaching some material. Additionally, the suction-based approach appears impractical for effective removal of material along a long narrow device with openings spaced along its length. The Palmer tool does not provide any direct volumetric control of the quantity of material removed. The Palmer tool also does not appear to provide removable or disposable material removing elements.

U.S. Patent Application Publication No. 2010/0262147 to Siegal et al. proposes a tissue removal device in which an elongated element is formed by a plurality of interconnected hollow segments connected by effective hinges. The elongated element assumes a material removing configuration in which a segment hinges to expose a cutting configuration of the segment. The hollow interior of the segment collects material during progressive formation of the material removing configuration. While the Siegal device provides a more predictable path and reduces the need for suction, its segments reduce flexibility making it difficult to reach some material. The device must be continually withdrawn from the surgical area to remove the material from the segments and does not appear to provide removable or disposable material removing elements.

There is therefore a need for a device for insertion into a body via an opening, and for removing material from within the body, which would follow a predefined path, provide flexibility to remove difficult to reach material, and reduce the frequency of insertion and removal of the device. There is also a need for a device that utilizes reduced cost and disposable elements.

SUMMARY

An instrument for removing material from within the body includes a distal portion that includes an adjustable length relative to a proximal portion and a flexible member that circulates through the distal portion. The exposed portion of the flexible member extends from the distal portion to remove the material.

In other features, the exposed portion includes an adjustable dimension that depends on the length of the distal portion. Adjustment of the length alters a shape of the exposed portion. The exposed portion forms a loop having an adjustable circumference. The distal portion slides along a concentric axis relative to the proximal portion to adjust the amount of the exposed portion. The distal portion rotates about a concentric axis relative to the proximal portion to rotate the exposed portion. The flexible member includes a plurality of teeth to engage the material. The distal portion includes an ingress channel and an egress channel through which the flexible member circulates. The instrument includes a container for receiving the material removed by the flexible member. The flexible member includes a plurality of cutting members attached to a flexible wire.

A method for removing material from within the body includes the steps of inserting an instrument into the body having a distal portion that includes an adjustable length relative to a proximal portion and circulating a flexible member through the distal portion. An exposed portion of the flexible member extends from the distal portion to remove the material from the body.

In other features, the method includes the steps of adjusting the length of the distal portion to adjust an amount of the exposed portion that extends from the distal portion, sliding the distal portion along a concentric axis relative to the proximal portion to adjust an amount of the exposed portion, and rotating the distal portion about a concentric axis relative to the proximal portion to rotate the exposed portion. The method includes capturing the material in a container of the instrument. The method includes calculating an amount of the material removed by the flexible member. The method includes removing disc material from an intervertebral disc space. The method includes calculating an amount of the material removed based on a weight of the material collected in a container of the instrument. The method includes calculating an amount of the material removed based on a weight of the material collected in a container of the instrument and an amount of fluid circulated through the instrument.

An instrument for removing material from a vertebral body includes a distal portion for insertion into the vertebral body and a proximal portion attached to a handle for adjusting a length of the distal portion relative to the proximal portion, a flexible wire that circulates through an ingress channel and an egress channel of the distal portion, an adjustable loop formed from a portion of the flexible wire that extends outside the distal portion, wherein a size of the loop depends on the length of the distal portion, a plurality of teeth on the loop for removing material from the vertebral body, a drive system that circulates the flexible wire, and a container for receiving the material removed by the teeth.

DETAILED DESCRIPTION

The instrument and method of the present follows a predefined path, provides flexibility to remove difficult to reach material, and reduces the frequency of insertion and removal of the device. The instrument utilizes reduced cost and disposable elements. The instrument comprises a housing having a distal end for insertion into the body and a handle and a flexible member that circulates through the housing. A portion of the flexible member forms an adjustable loop that extends from the distal end to remove the material. The housing provides a predetermined path for the circulating loop while the adjustable loop provides flexibility to remove material throughout the surgical area. In some examples, the flexible member may be removable and disposable.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 1:
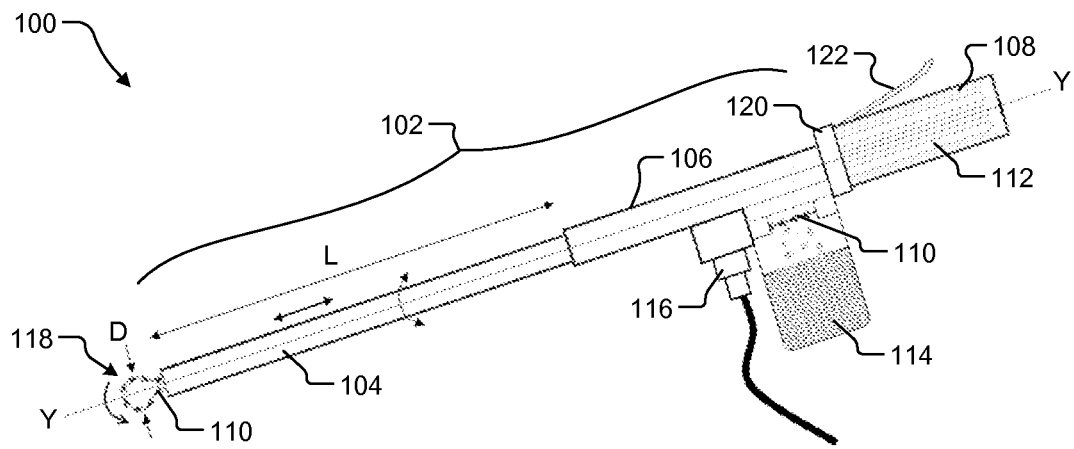
FIGS. 1-2B are elevational side views of an exemplary instrument for removal of material within a body according to the principles of the present disclosure.
Figure 6A:
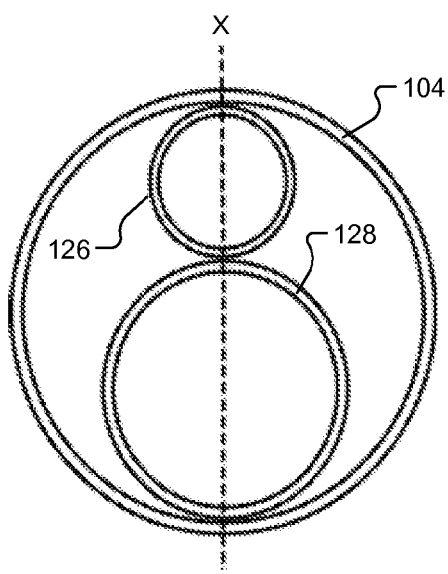
FIGS. 6A and 6B are cross-sectional views of a distal portion of the instrument illustrating exemplary passageways that guide the flexible member through the instrument.
Figure 6B:
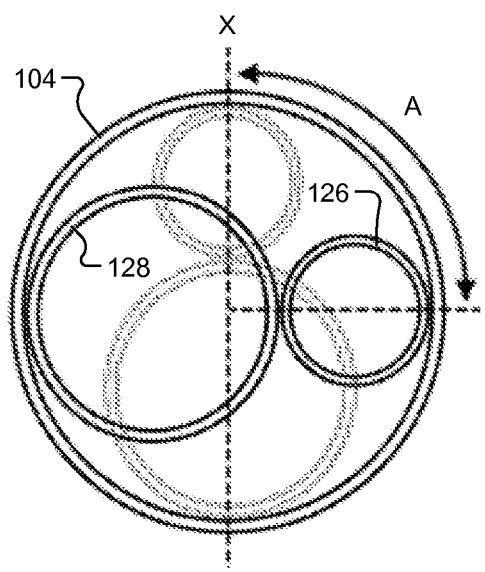

FIG. 1 illustrates an exemplary instrument 100 for removal of material from within a body according to the principles of the present disclosure. The instrument 100 includes a housing 102, a distal portion 104, and a proximal portion 106. A surgeon may grasp a handle 108 on the proximal portion 106 to maneuver the distal portion 104 inside the surgical area of a patient. In one example, the surgeon may use the instrument 100 to remove material from a vertebral body 200 (see FIGS. 3A-4D). In other examples, the instrument 100 may be used to remove material from various regions of the body, and in particular, where minimally invasive surgery (MIS) is advantageous. The distal portion 104 may slide along a common concentric axis Y relative to the housing 102. The distal portion 104 may include an adjustable length L. For example, the distal portion 104 may telescope within the housing 102. The distal portion may rotate about the axis Y relative to the housing 102. The distal portion 104 may include an adjustable angle A as illustrated in FIGS. 6A-6B. For example, the distal portion 104 may rotate within the housing 102.

A flexible member 110 circulates through the distal portion 104 and exits through a distal end of the distal portion 104. Upon insertion into the surgical area of the body, such as the vertebral body 200 in FIGS. 3A-4D, the flexible member 110 may remove material from the body. For example, the flexible member may remove disc annulus and/or nucleus material. The flexible member 110 may include a wire, cable, or fibrous winding comprised of materials such as steel, nylon, or another flexible and durable material. The flexible member 110 may be molded as a single piece, braided together, and/or welded. The flexible member 110 may include a continuous band or coil of cable that circulates within the instrument 100. In one example, the flexible member 110 includes a disposable cable. In another example, the flexible member 110 forms a continuous belt by joining two ends of the flexible member. In other examples, the flexible member 110 includes two non-joined ends that may exit the housing 102 through various apertures. The flexible member 110 may circulate through other portions of the instrument including the housing 102 and the proximal portion 106.

A drive system 112 circulates the flexible member 110 through the distal portion 104. The drive system 112 may include a pneumatic drive, electric drive, manual drive, or other drive systems routinely found in a surgical setting. The drive system 112 may include a drive gear (not shown) that engages the flexible member 110. For example, the drive gear may include slotted teeth that engage a portion of the flexible member 110. In various examples, portions of the drive system 112 may be integrated within the housing 102 and the proximal portion 106.

A container 114 collects material removed by the flexible member. The container 114 may be in communication with the housing 102 and/or distal portion 104 such that the flexible member 110 may circulate through a portion of the container 114. The container 114 may be removable for disposal of material removed by the flexible member 110. The container 114 may measure the amount of material removed from the body. A cleaner 116 may remove the material from the flexible member 110 for deposit within the container 114. Portions of the cleaner 116 may be in communication with the container 114 and/or disposed within the container 114. The cleaner 116 may include a blower that applies a jet of gas or fluid to the flexible member 110 to blow material off of the flexible member 110. In other examples, portions of the cleaner 116 may directly engage the flexible member 110 to brush material off of the flexible member 110.

Figure 2A:
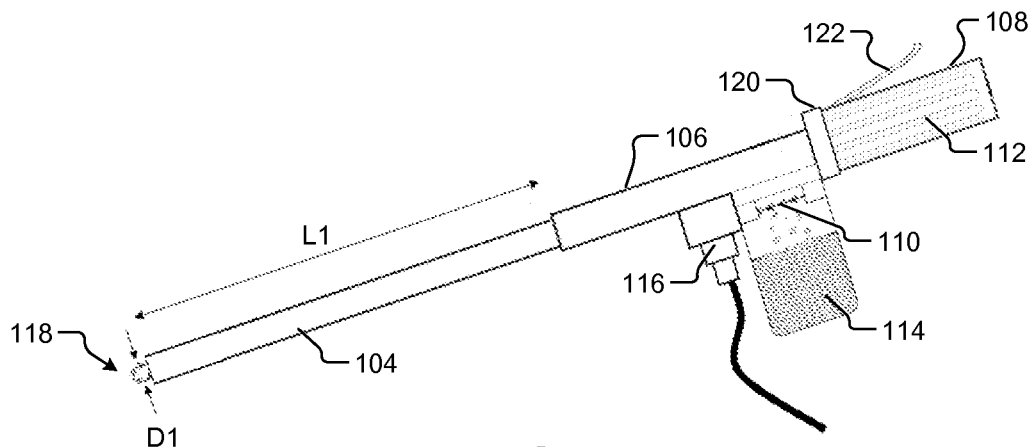
Figure 2B:
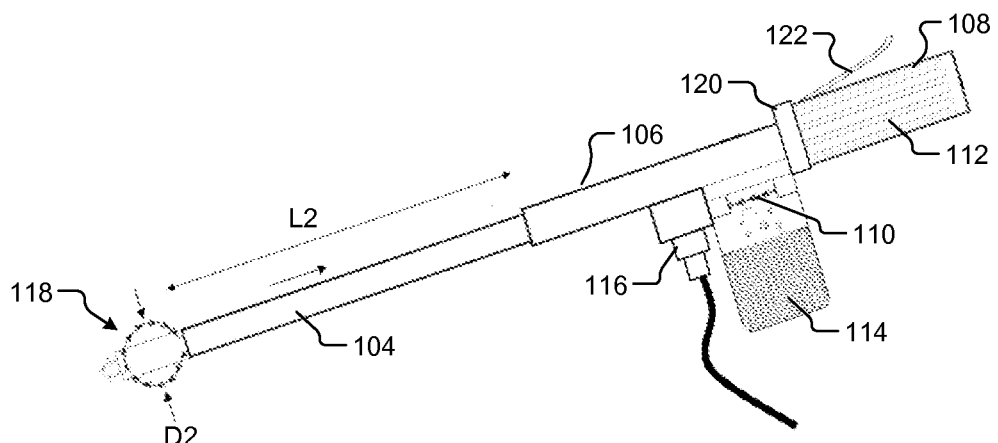

The distal portion 104 may be advanced and retracted relative to the housing 102 in order to vary an amount of the flexible member 110 that extends outside the distal end of the distal portion. For example, the amount of the flexible member 110 that extends outside the distal end may form an adjustable loop 118. As the length L of the distal portion 104 increases, more of the flexible member 110 remains within the distal portion 110 resulting in a smaller loop 118 as illustrated in FIG. 2A. That is, when the distal portion 104 includes a first length L1, the adjustable loop 118 includes a first dimension D1. As the length L of the distal portion 104 decreases, less of the flexible member 110 remains within the distal portion 110 resulting in a larger loop 118 as illustrated in FIG. 2B. That is, when the distal portion 104 includes a second length L2, the adjustable loop 118 includes a second dimension D2. In the examples of FIGS. 2A and 2B, the length may decrease from L1 to L2 while the dimension increases from D1 to D2.

The adjustable loop 118 may include an irregular shape other than a circle as illustrated in the figures of the present disclosure. The flexible member 110 may include flexible properties that enable formation of various shapes and dimensions of the adjustable loop 118 to conform substantially to the interior spaces between adjacent vertebrae. For example, the adjustable loop 118 may include an adjustable diameter D. In other examples, the adjustable loop 118 may include an adjustable length or circumference of the flexible member 110 that extends outside the distal portion 104. Dimensions of the adjustable loop 118 may decrease in size to conform to a radial path of the flexible member 110 around the distal end of the distal portion 104. Dimensions of the adjustable loop 118 may increase in size to fill the entire space occupied by the vertebral body 200 as described with reference to FIGS. 3A-4D below.

The instrument 100 may include various controls for maneuvering the distal portion 104. In FIGS. 1-2B, the proximal portion 106 includes a loop controller 120 to adjust the dimensions of the loop 118 and a speed controller 122 to adjust the speed of the flexible member 110 through the instrument 100. The loop controller 120 may include a thumbwheel that rotates in a first direction to advance the distal portion 104 relative to the housing 102 and a second direction to retract the distal portion 104 relative to the housing 102. The distal portion 104 may include a threaded end (not shown) that engages with threading on the thumbwheel to advance and retract. The speed controller 122 may include a spring loaded switch that adjusts features of the drive system 112 to control the speed of the flexible member 110. The speed controller 122 may adjust a resistance of an electric drive system, a flow rate of a pneumatic drive system, or other features to increase or decrease the speed of the flexible member 110.

Figure 3A:
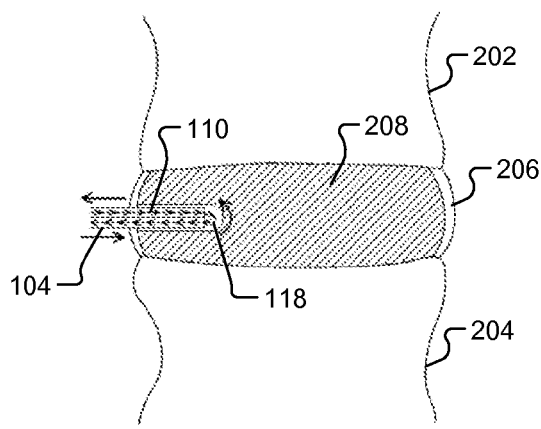
FIGS. 3A-3F are a series of cross-sectional views in a coronal plane illustrating actuation of the instrument for removal of material from within a vertebral body according to the principles of the present disclosure.
Figure 3B:
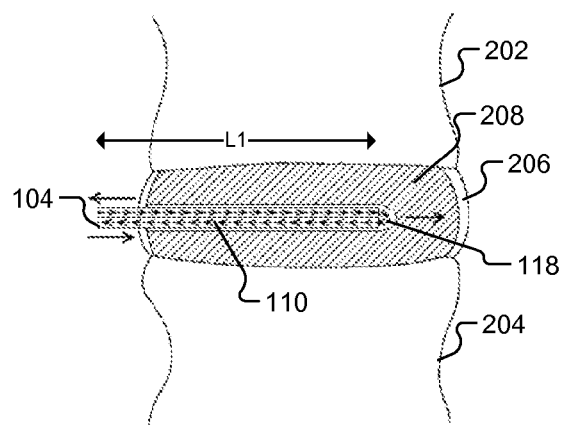

FIGS. 3A-3F illustrate a method of removing material from within the body using the instrument 100 of FIGS. 1-2B in the coronal plane. The distal portion 104 of the instrument 104 may be inserted between two vertebrae 202 and 204. For difficult to puncture regions of the vertebral body 200, such as the annulus of the annulus 206, a pilot hole may be required. In FIG. 3A, the flexible member 110 begins to circulate in and advance into the interior nucleus 208 of the vertebral body 200. Initially, the dimensions of the loop 118 may be at a minimum to enable easier insertion into the vertebral body 200. For example, the loop may include the first diameter D1 and the distal portion 104 may include the first length L1 as illustrated in FIG. 2A. Continuing with FIG. 3B, the surgeon advances the distal portion 104 further into the nucleus 208. As the distal portion 104 advances through the vertebral body 200, material may be removed and transported back to the container 114.

Figure 3C:
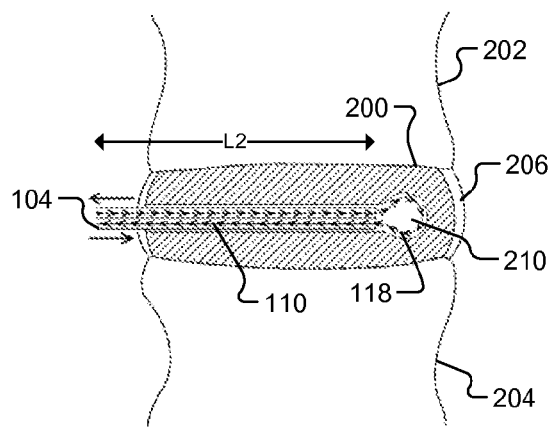
Figure 3D:
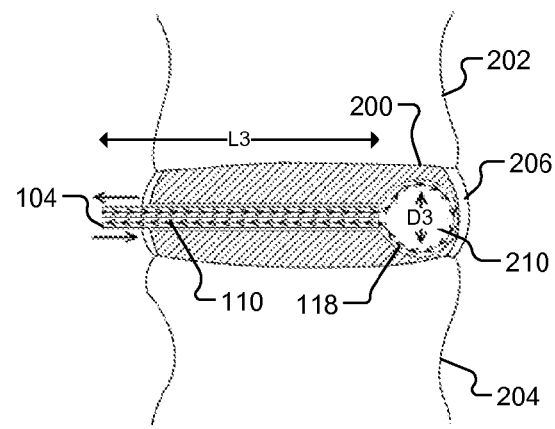

In FIG. 3C, the surgeon may begin to decrease the length of the distal portion 104 to L2 and thus, increase the diameter of the loop 118 to the second diameter D2 as illustrated in FIG. 2B. The loop 118 continues to remove additional material from the vertebral body 200 creating a cavity 210 with similar dimensions as the loop 118. The surgeon may continue to decrease the length of the distal portion 104 to L3, a minimum length of the distal portion 104 as shown in FIG. 3D. The loop 118 increases to a maximum diameter D3 and further enlarges the cavity 210. The maximum diameter D3 may correspond to a maximum thickness of the vertebral body 200.

Figure 3E:
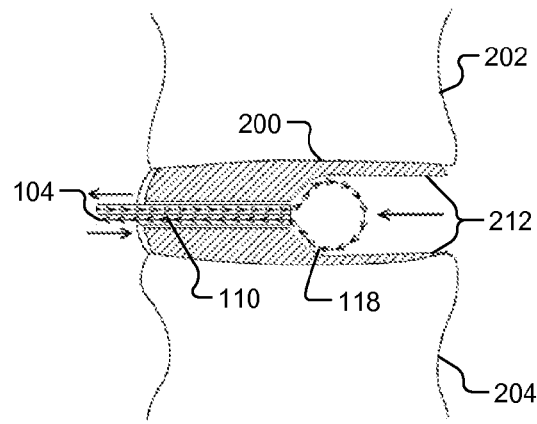
Figure 3F:
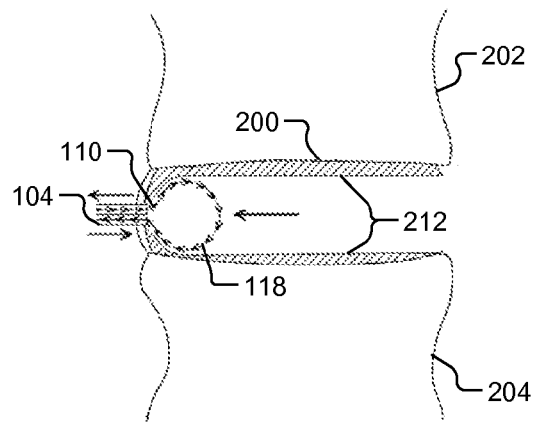
Figure 4A:
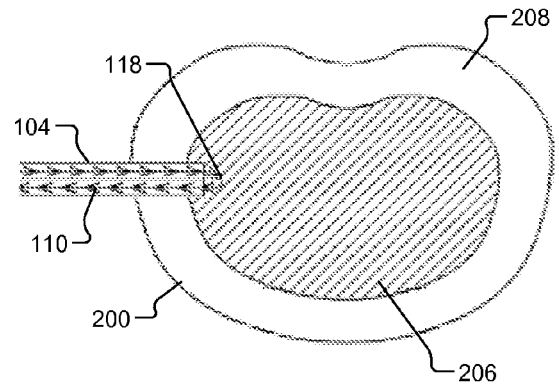
FIGS. 4A-4D are a series of cross-sectional views in a transverse plane illustrating actuation of the instrument for removal of material from within a vertebral body according to the principles of the present disclosure.
Figure 4B:
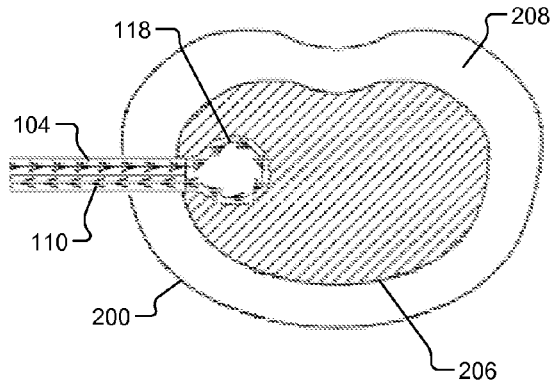
Figure 4C:
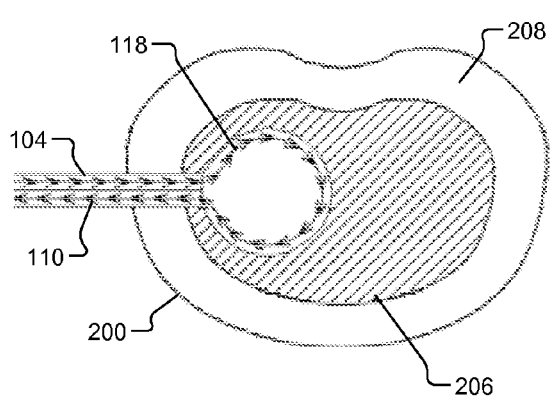
Figure 4D:
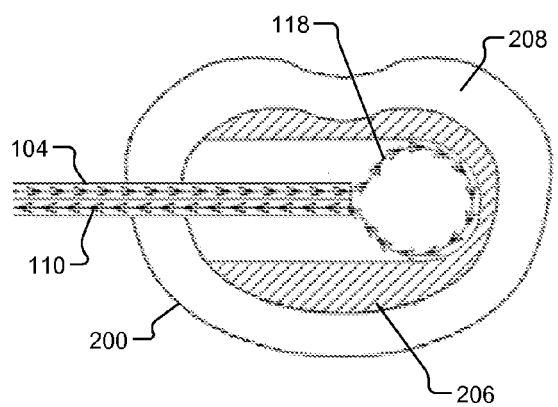

Continuing with FIGS. 3E and 3F, the surgeon may begin to remove the distal portion 104 from the vertebral body 200. As the distal portion 104 retracts from the space between the vertebrae 202 and 204, the loop 118 clears a channel 212 from the vertebral body 200. The channel 212 may include dimensions corresponding to the dimensions of the loop 118 and the path of removal. The surgeon may repeat the process to ensure complete removal of material from the vertebral body 200. Depending on the consistency and structure of the material to be removed, various flexible members 110 with different material removing elements may be required.

FIGS. 4A-4D illustrate the method corresponding to the above description with reference to FIGS. 3A-3F. In FIGS. 4A-4D, the plane in which the loop 118 circulates has been shifted by approximately 90 degrees to reflect removal of material from the vertebral body 200 in a transverse plane. The surgeon may rotate the instrument 100 by 90 degrees to remove the material. In other examples, the distal portion 104 may rotate relative to the housing 102. The flexible member 110 may travel within passageways inside the distal portion 104 as illustrated in FIGS. 6A and 6B. The passageways may include channel separated by a wall, cannulae, tubes, sheaths, etc. For example, the distal portion 104 may include an egress passageway 126 and an ingress passageway 128. The flexible member 110 may exit the distal portion 104 through the egress passageway 126. The flexible member 110 may return into the portion 104 through the ingress passageway 128.

The ingress passageway 128 may include a larger diameter than the egress passageway 126 to accommodate the added volume of material removed by the flexible member 110. In a first configuration shown in FIG. 6A, the passageways 126 and 128 may be stacked along an axis X corresponding to removal of material in the coronal plane of FIGS. 3A-3F. In a second configuration shown in FIG. 6B, the passageways 126 and 128 may be rotated approximately 90 degrees clockwise corresponding to removal of material in the transverse plane of FIGS. 4A-4D. The distal portion 104 may rotate through various angles A. The flexibility of the flexible member 110 allows for some twisting of inside the distal portion 104. Alternately, a portion of the drive system 112 may rotate with the distal portion 104 to reduce twisting of the flexible member 110.

Figure 5A:
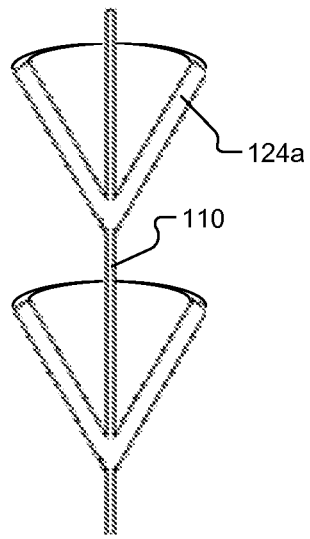
FIGS. 5A-5C are partial cross-sectional views of exemplary material removal elements on a flexible member that circulate through the instrument according to the principles of the present disclosure.
Figure 5B:
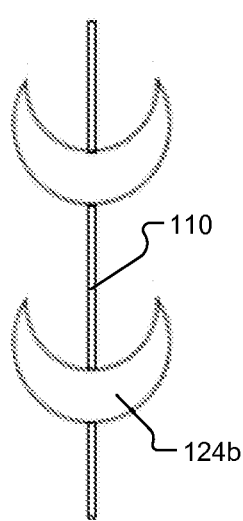
Figure 5C:
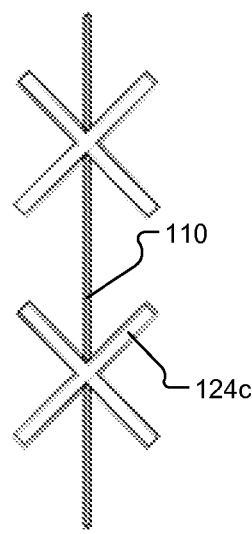

Referring now to FIGS. 5A-5C, a plurality of material removing elements 124 may be attached to the flexible member 110 to cut, pull, shred, and grasp material from inside the body. For example, the material removing elements 124 may be configured to remove fibrous and cartilaginous material from a vertebral body disposed between two adjacent vertebrae. In one example, the material removing elements 124 may include V-shaped or conical cups 124a as shown in FIG. 5A. The cups 124a may include sharp edges for cutting and/or scraping away more fibrous material. The cups 124a may scoop out the material and carry at least a portion of the material back through the distal portion 104 to the container 114. In another example, the material removing elements may include cutters 124b as shown in FIG. 5B. The cutters 124b may cut pieces of material loose from the vertebral body 200 for removal by suction or vacuum. In another example, the material removing elements 124 may include barbs 124c as shown in FIG. 5C. The barbs 124c may catch looser strands of fibrous material left behind from the cutters 124b. The barbs 124c may grasp onto the strands and pull the strands back through the distal portion 104 to the container 114. Various additional material removing elements 124 may be used to cut, pull, shred, scrape, and/or grasp remaining material.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. An instrument for removing material from within a body, comprising:
   a distal portion that includes an adjustable length relative to a proximal portion; and
   a flexible member that circulates through the distal portion, wherein an exposed portion of the flexible member extends from the distal portion to remove the material, wherein the exposed portion includes an adjustable dimension that depends on the length of the distal portion.

2. The instrument of claim 1, wherein adjustment of the length alters a shape of the exposed portion.

3. The instrument of claim 1, wherein the exposed portion forms a loop having an adjustable circumference.

4. The instrument of claim 1, wherein the distal portion slides along a concentric axis relative to the proximal portion to adjust the amount of the exposed portion.

5. The instrument of claim 1, wherein the distal portion rotates about a concentric axis relative to the proximal portion to rotate the exposed portion.

6. The instrument of claim 1, wherein the flexible member includes a plurality of teeth to engage the material.

7. The instrument of claim 1, wherein the distal portion includes an ingress channel and an egress channel through which the flexible member circulates.

8. The instrument of claim 1, further comprising a container for receiving the material removed by the flexible member.

9. The instrument of claim 1, wherein the flexible member includes a plurality of cutting members attached to a flexible wire.

10. A method for removing material from within a body, comprising:
    inserting an instrument into the body having a distal portion that includes an adjustable length relative to a proximal portion; circulating a flexible member through the distal portion, wherein an exposed portion of the flexible member extends from the distal portion to remove the material from the body; and adjusting the length of the distal portion to adjust an amount of the exposed portion that extends from the distal portion.

11. The method of claim 10, further comprising sliding the distal portion along a concentric axis relative to the proximal portion to adjust an amount of the exposed portion.

12. The method of claim 10, further comprising rotating the distal portion about a concentric axis relative to the proximal portion to rotate the exposed portion.

13. The method of claim 10, further comprising capturing the material in a container of the instrument.

14. The method of claim 10, further comprising removing disc material from an intervertebral disc space.

15. An apparatus for removing material from within an intervertebral disc body, comprising:
    a distal portion that includes an adjustable length relative to a proximal portion and an ingress channel and an egress channel; and
    a flexible member that circulates through the ingress channel and the egress channel of the distal portion, wherein an exposed portion of the flexible member extends from the distal portion to remove the material, wherein the exposed portion includes an adjustable dimension that depends on the length of the distal portion.

16. The apparatus of claim 15, wherein the flexible member includes a continuous member that circulates within the instrument and configured to form the exposed portion as an adjustable loop.

17. The apparatus of claim 16, wherein increasing the length of the distal portion causes more of the flexible member to remain within the distal portion and decreases a size of the adjustable loop.

18. The apparatus of claim 16, wherein decreasing the length of the distal portion causes less of the flexible member to remain within the distal portion and increases a size of the adjustable loop.

* * * * *